(12) United States Patent
Sutton et al.

(10) Patent No.: US 9,758,758 B2
(45) Date of Patent: Sep. 12, 2017

(54) **ISOLATED STRAIN OF *CLONOSTACHYS ROSEA* FOR USE AS A BIOLOGICAL CONTROL AGENT**

(71) Applicant: Bee Vectoring Technology Inc., Mississauga (CA)

(72) Inventors: John Sutton, Ariss (CA); Todd Gordon Mason, Oakville (CA)

(73) Assignee: Bee Vectoring Technology Inc., Mississauga, ON (CA)

( * ) Notice: Subject to any disclaimer, the term of this patent is extended or adjusted under 35 U.S.C. 154(b) by 0 days.

(21) Appl. No.: 15/021,425

(22) PCT Filed: Sep. 11, 2014

(86) PCT No.: PCT/CA2014/000683
§ 371 (c)(1),
(2) Date: Mar. 11, 2016

(87) PCT Pub. No.: WO2015/035504
PCT Pub. Date: Mar. 19, 2015

(65) Prior Publication Data
US 2016/0222342 A1 Aug. 4, 2016

Related U.S. Application Data

(60) Provisional application No. 61/876,469, filed on Sep. 11, 2013.

(51) Int. Cl.
| | | |
|---|---|---|
| *A01N 63/00* | (2006.01) |
| *C12N 1/14* | (2006.01) |
| *A01H 17/00* | (2006.01) |
| *A01N 63/04* | (2006.01) |
| *C12R 1/645* | (2006.01) |
| *A01N 25/22* | (2006.01) |

(52) U.S. Cl.
CPC .............. *C12N 1/14* (2013.01); *A01H 17/00* (2013.01); *A01N 25/22* (2013.01); *A01N 63/04* (2013.01); *C12R 1/645* (2013.01)

(58) Field of Classification Search
None
See application file for complete search history.

(56) References Cited

U.S. PATENT DOCUMENTS

| | | |
|---|---|---|
| 8,101,551 B2 | 1/2012 | Stewart et al. |
| 2012/0021906 A1 | 1/2012 | Sutton |

FOREIGN PATENT DOCUMENTS

| | | |
|---|---|---|
| JP | 2005 73586 A | 3/2005 |
| WO | 00/18241 A1 | 4/2000 |
| WO | 2007/107000 A1 | 9/2007 |
| WO | 2012/095431 A1 | 7/2012 |
| WO | 2012/135940 A1 | 10/2012 |
| WO | 2013/134870 A1 | 9/2013 |
| WO | 2014/117278 A1 | 8/2014 |

OTHER PUBLICATIONS

Rodriguez, M.A., et al., "Clonostachys rosea BAFC3874 as Sclerotinia sclerotiorum antagonist mechanisms involved and potential as a biocontrol agent." Journal of Applied Microbiology, May 2011, vol. 110, pp. 1177-1186.
International Search Report (dated Nov. 24, 2014) and Written Opinion (dated Dec. 11, 2014) for corresponding PCT Application No. PCT/CA2014/000683.
Sutton, et al., "Gliocladium roseum: a versatile adversary of Botrytis cinerea in crops." Plant Disease, 1997, vol. 81, No. 4, pp. 316-328.
Sutton, et al., "Ability of Clonostachys rosea to establish and suppress sporulation potential of Botrytis cinerea in deleafed stems of hydroponic greenhouse tomatoes." Biocontrol Sci Technol, 2002, 12(4), pp. 413-425.
Sutton, et al., "Evaluation of the Fungal Endophyte Clonostachys rosea as an Inoculant to Enhance Growth, Fitness and Productivity of Crop Plants." Proc. IVth IS on Seed, Transplant and Stand Establishment of Hort. Crops Ed.: D.I. Leskovar, Acta Hort. 782, ISHS 2008, pp. 279-286.
Xue, A., "Biological Control of Pathogens Causing Root Rot Complex in Field Pea Using Clonostachys rosea Strain ACM941." The American Phytopathological Society, 2003, vol. 93, No. 3, pp. 329-335.
Kapongo, J.P., et al., "Co-vectoring of Beauveria bassiana and Clonostachys rosea by bumble bees (*Bombus impatiens*) for control of insect pests and suppression of grey mould in greenhouse tomato and sweet pepper." Biological Control, 2008, vol. 46, No. 3, pp. 508-514.
Shafia, A., et al. "Influence of preinoculation light intensity on development and interactions of Botrytis cinerea and Clonostachys rosea in tomato leaves." Canadian Journal of Plant Pathology, 2001, vol. 23, pp. 346-357.
Roberti, R., et al., "Induction of PR proteins and resistance by the biocontrol agent Clonostachys rosea in wheat plants infected with Fusarium culmorum." Plant Science, 2008, vol. 175, No. 3, pp. 339-347.
Toledo, A.V., et al., "First record of Clonostachys rosea (Ascomycota: Hypocreales) as an entomopathogenic fungus of Oncometopia tucumana and Sonesimia grossa (Hemiptera: Cicadellidae) in Argentina." Journal of Invertebrate Pathology, 2006, vol. 92, No. 1, pp. 7-10.
Nobre, S., et al., "Selection of Clonostachys rosea isolates from Brazilian ecosystems effective in controlling Botrytis cinerea." Biological Control, 2005, vol. 34, No. 2, pp. 132-143.
Moeller, K., et al., "Biocontrol of Pythium tracheiphilum in Chinese Cabbage by Clonostachys rosea under Field Conditions." Biocontrol Science and Technology, 2003, vol. 13, pp. 171-182.
Jensen, B., et al., "Biological seed treatment of cereals with fresh and long-term stored formulations of Clonostachys rosea: Biocontrol efficacy against Fusarium culmorum." European Journal of Plant Pathology, 2000, vol. 106, No. 3, pp. 233-242.
Palazzini, J.M., et al., "Biocontrol and population dynamics of *Fusarium* spp. on wheat stubble in Argentina." Plant Pathology, 2013, vol. 62, No. 4, pp. 859-866.

(Continued)

*Primary Examiner* — Kade Ariani
(74) *Attorney, Agent, or Firm* — Bereskin & Parr LLP/S.E.N.C.R.L., s.r.l.; I. Laurence MacPhie

(57) ABSTRACT

Described is an isolated strain of the fungus *Colonostachys rosea* termed BVT Cr-7 useful as a biological control agent for the treatment of plants. The isolated strain, formulations comprising said strain and/or spores derived from said strain may be applied to plants or plant materials in order to improve plant yield, to improve plant growth, or for the treatment or prevention of diseases or pathogens in the plant.

21 Claims, No Drawings

(56) References Cited

OTHER PUBLICATIONS

Moraga-Suazo, P., et al., "Evaluation of *Trichoderma* spp. and *Clonostachys* spp. strains to control fusarium circinatum in pinus radiata seedlings." Chilean Journal of Agricultural Research, 2011, 71(3), pp. 412-417.

Krauss, U., et al., "Interaction between the entomopathogens beauveria bassiana, metarhizium anisopliae and paecilomyces fumosoroseus and the *Mycoparasites clonostachys* spp., trichoderma harzianum and lecanicillium lecanii." Biocontrol Science and Technology, 2004, vol. 14, No. 4, pp. 331-346.

Supplementary European Search Report for corresponding European Patent Application EP 14 84 3455 dated Jan. 13, 2017.

English Abstract of JP 2005 073586, Shizuoka Prefecture, published Mar. 24, 2005.

ISOLATED STRAIN OF *CLONOSTACHYS ROSEA* FOR USE AS A BIOLOGICAL CONTROL AGENT

CROSS REFERENCE TO RELATED APPLICATIONS

This application is a national phase entry of PCT/CA2014/000683 filed Sep. 11, 2014 (which designates the U.S.) which claims priority to US Provisional Patent Application Ser. No. 61/876,469, filed Sep. 11, 2013, the contents of which are hereby incorporated by reference in their entirety

FIELD

The present disclosure relates to an isolated strain of the fungus *Clonostachys rosea* and more specifically to an isolated strain of *Clonostachys rosea* useful as a biological control agent for the treatment of plants.

BACKGROUND

*Clonostachys rosea f. rosea* is a beneficial micro-fungus which is found within the tissues of a diversity of plants in the wild and in almost all species of crop plants. The fungus is common in healthy roots, leaves, stems, flowers, and fruits of plants collected on farms and in nurseries, orchards, vineyards, pastures, and gardens around the world. It has been reported in plants and soils from regions as diverse as the sub-arctic, cool and warm temperate zones, deserts and the humid tropics. Plants colonized by *C. rosea* do not show any visual signs that the fungus is present until the tissues naturally senesce and die. At that time the fungus may sporulate and whitish growth may become visible on plant surfaces, especially with the aid of a hand lens. Unlike pathogenic organisms associated with disease, *Clonostachys* does not cause lesions, spotting, wilting or other symptoms in plants. *Clonostachys rosea f. rosea* is also known to be a beneficial biological control agent for the treatment of plants and helps to protect plants against diseases and environmental stresses, and in promoting plant growth and productivity.

Stewart et al. (U.S. Pat. No. 8,101,551) describes *Clonostachys rosea* strain 88-710 and refers to the strain having benefits for the promotion of plant vigor, health, growth and yield.

There remains a need for new strains of *Clonostachys rosea* that are useful as biological control agents for the treatment of plants.

SUMMARY

The inventors have isolated and characterized a new strain of the fungus *Clonostachys rosea f. rosea*. As described herein, this new strain of *Clonostachys rosea* f. *rosea* designated "BVT Cr-7" is particularly useful as a biological control agent for the treatment of plants. In one aspect of the disclosure, an isolated culture of *Clonostachys rosea* f. *rosea* strain BVT Cr-7 has been deposited under accession number 040913-01 at the International Depository Authority of Canada located at the National Microbiology Laboratory, Public Health Agency of Canada, 1015 Arlington Street, Winnipeg, Manitoba, R3E 3R2, Canada on Sep. 4, 2013.

As set out in Example 1, a series of different strains of *Clonostachys rosea* f. *rosea* were isolated and characterized in order to identify strains with particularly advantageous properties for use as a biological control agent. In comparison to other strains of *Clonostachys rosea* f. *rosea*, BVT Cr-7 demonstrated a number of improved properties and/or combination of desirable properties for use as a biological control agent. For example, BVT Cr-7 demonstrated improved or desirable properties with respect to the growth and abundance of spore production, its ability to establish endophytically inside a diverse range of plants, including in the roots of crop plants and in the flowers and foliage of test plants and its ability to suppress or control a wide spectrum of plant diseases and/or pathogens. In one embodiment, BVT Cr-7 shows one or more improved properties compared to a control strain of *Clonostachys rosea f. rosea*, such as 88-710 and/or EV1a.

Furthermore, as set out in Examples 2-5, the application of BVT Cr-7 to plants in field trials as well as in greenhouses under controlled conditions demonstrates that BVT Cr-7 is a broad spectrum biological control agent with high performance against a number of different diseases, under diverse conditions and for a wide variety of plants. As shown in Example 4, BVT Cr-7 is also useful for reducing the spoilage of plant materials such as by reducing the levels of rot or discoloration in harvested crops.

Accordingly, in one aspect there is provided an isolated culture of *Clonostachys rosea f. rosea* strain BVT Cr-7 as described herein. In one embodiment, the strain is that deposited under accession number 040913-01 at the International Depository Authority of Canada located at the National Microbiology Laboratory, Public Health Agency of Canada, 1015 Arlington Street, Winnipeg, Manitoba, R3E 3R2, Canada on Sep. 4, 2013.

Also provided are spores generated from *Clonostachys rosea f. rosea* strain BVT Cr-7, as well as progeny of *Clonostachys rosea f. rosea* strain BVT Cr-7 and formulations containing isolated cultures, spores and/or progeny of BVT Cr-7. Also provided is an isolated cell of *Clonostachys rosea f. rosea* strain BVT Cr-7 that is able to reproduce asexually. In one embodiment, there is provided a spore obtained by incubating an isolated culture of BVT Cr-7 on a substrate under conditions suitable for sporulation. In one embodiment, there is provided a formulation comprising spores of BVT Cr-7 that are bound to a stabilizing agent, such as calcium silicate.

In one embodiment, the isolated culture of BVT Cr-7 described herein colonizes plants as an endophyte. In one embodiment, contacting a plant with BVT Cr-7 suppresses or controls a disease or pathogen that affects the foliage, flowers, fruits and/or roots of the plant. In one embodiment, the disease is grey mold disease, white mould disease, brown rot, root rot and/or phomopsis. In one embodiment, the disease is caused by *Botrytis cinerea*, *Sclerotinia sclerotiorum* and/or by species of *Pythium* spp., *Rhizoctonia*, and/or *Fusarium*.

In one embodiment, there is also provided a plant or plant material that has been colonized with an inoculum of BVT Cr-7.

In one embodiment, *Clonostachys rosea f. rosea* strain BVT Cr-7 is useful as a biological control agent for the treatment of plants. In one embodiment, there is provided a method for the treatment of a plant comprising contacting the plant with *Clonostachys rosea f. rosea* strain BVT Cr-7 as described herein. For example, in one embodiment BVT Cr-7 is useful for improving the health, growth, and/or yield of the plant relative to a control plant that has not been treated with BVT Cr-7. In one embodiment, BVT Cr-7 is useful for the prevention or treatment of diseases and/or pathogens in a plant. In one embodiment, BVT Cr-7 is useful to promote the exclusion of other fungi, including pathogenic fungi, from colonizing a plant. In one embodiment, BVT Cr-7 is useful for triggering natural resistance to diseases and stresses in a plant, such as in response to infection with a pathogen. Also provided is a method for reducing the spoilage of a plant material comprising contacting the plant material with BVT Cr-7.

In one embodiment, BVT Cr-7 is useful for the treatment of a plant to prevent or treat diseases and/or pathogens that may affect the health, growth and/or yield of the plant. In one embodiment, the pathogen is a microorganism, such as a fungus or bacteria. Examples of pathogens that may affect the health, growth and/or yield of a plant that may be controlled by BVT Cr-7 include, but are not limited to, *Botrytis cinerea, Sclerotinia sclerotiorum, Pythium* spp., *Alternaria, Monilia, Monilinia, Colletotrichum, Cladosporium Rhizoctonia, Streptomyces, Didymella* and/or *Fusarium*. Examples of diseases that may affect the health, growth and/or yield of a plant that may be controlled by BVT Cr-7 application include, but are not limited to grey mold disease, white mould disease, brown rot and/or root rot. Other examples include *phomopsis* diseases in e.g., blueberries or grapes, and potato scab.

In one embodiment, the plant is any plant or part thereof that can be colonized endophytically by *Clonostachys rosea f. rosea* strain BVT Cr-7. In one embodiment, the plant is a flowering plant, cereal, legume, or vegetable plant. For example, in one embodiment, the methods and uses described herein are useful for the treatment of plants such as flowering plants or crops such as vegetables, fruits, cereals, as well as seeds or seedlings thereof. In one embodiment, the methods and uses described herein are useful for the treatment of and seedlings/transplants of coniferous trees. In one embodiment, the plant is a tree such as pine, black spruce or pine transplants. In one embodiment, the plant is wheat, barley, sunflower, canola, blueberries, strawberries, raspberries, grapes, potatoes, peppers, cucumbers, tomatoes, turf grasses, peppers, tomatoes, cucumbers, broccoli, cauliflower, peaches, apple, canola, flowering ornamentals such as roses, geraniums, cyclamen, snapdragon, Exacum, begonia or lilies. In one embodiment, the plant is grown outdoors. In one embodiment, the plant is grown in a greenhouse.

In one embodiment, the methods and uses described herein comprise contacting the plant with BVT Cr-7, such as a BVT Cr-7 culture, spore, or formulation thereof. In one embodiment, the BVT Cr-7 culture, spore, or formulation thereof is useful as an inoculant. In some embodiments, BVT Cr-7 is applied to a plant or part thereof as a spray, mist, dip, powder, or nutrient solution and/or through insect vectoring, such as by use of bee vectoring as described in PCT Application No. PCT/CA2013/050179, hereby incorporated by reference in its entirety.

Also provided are methods for the production of a biological control agent, the method comprising inoculating a substrate with an isolated culture BVT Cr-7 and incubating the substrate under conditions suitable for fungal growth to produce *Clonostachys rosea f. rosea* strain BVT Cr-7. Optionally, the method further comprises incubating the substrate under conditions suitable for fungal sporulation and removing the spores from the substrate to produce an inoculum.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

DETAILED DESCRIPTION

Definitions

As used herein "*Clonostachys rosea f. rosea* strain BVT Cr-7" or "BVT Cr-7" refers to the fungus strain deposited under accession number 040913-01 at the International Depository Authority of Canada located in the National Microbiology Laboratory, Public Health Agency of Canada, 1015 Arlington Street, Winnipeg, Manitoba, R3E 3R2, Canada on Sep. 4, 2013. The terms "*Clonostachys rosea f. rosea* strain BVT Cr-7", "BVT Cr-7" or "*Clonostachys rosea f. rosea* strain IDAC 040913-01" also includes isolates of said strain or any cells, cultures, spores, and progeny produced from said strain, such as by asexual reproduction.

Different methods known in the art may be used for culturing BVT Cr-7 or preparing fungal spores, including but not limited to the methods described herein and in Sutton et al. "*Gliocladium roseum*: a versatile adversary of *Botrytis cinerea* in crops." Plant Dis 1997; 81:316-28; Sutton et al. "Ability of *Clonostachys rosea* to establish and suppress sporulation potential of *Botrytis cinerea* in deleafed stems of hydroponic greenhouse tomatoes" *Biocontrol Sci Technol* 2002; 12(4):413-25, and US Patent Application No. 2012/0021906 "Fungal Inoculant Compositions" all of which are incorporated herein by reference in their entirety.

As used herein, "plant" refers to any member of the kingdom Plantae that is able to be colonized endophytically by BVT Cr-7. In a preferred embodiment, the plant is a cultivated plant. In one embodiment "plant" also includes tubers, seeds and/or seedlings that give rise to a plant and optionally includes plant material. As used herein "plant material" refers to any material that is harvested or separated from a plant and destined for use as a food or other uses that is susceptible to spoilage due to disease and/or infection by pathogens. Examples of plant material include, but are not limited to, harvested grains, fruits or vegetables.

As used herein "colonized endophytically" refers to the process by which spores of a fungus penetrate and form fungal colonies within a plant host, or part thereof, without causing symptoms or other aspects of disease, or otherwise harming the host.

As used herein, "biological control agent" refers to an agent that promotes the health, growth, vigor and/or yield of plants; enhances germination rates and/or seed quality; enhances resistance to disease, pests, and/or environmental stresses such as adverse weather or soil conditions; controls or acts against diseases or pathogens or is useful for the treatment or prevention of a disease or pathogen; or promotes the recovery of plants from injury and/or infection. A preferred example of a biological control agent is *Clonostachys rosea* BVT Cr-7 as described herein.

As used herein, "pathogen" refers to a microorganism that may invade and colonize a plant host and reduce the health, growth, vigor and/or yield of the plant. Examples of pathogens include, but are not limited to, bacteria and fungi such as *Botrytis cinerea Sclerotinia sclerotiorum*, and species of *Pythium, Alternaria, Monilia, Monilinia, Colletotrichum, Cladosporium Rhizoctonia, Streptomyces, Didymella* and/or *Fusarium*.

Interaction of *Clonostachys rosea* with Plants and Plant Disease Organisms

Without being limited by theory, it is believed that *Clonostachys rosea* BVT Cr-7 confers protection to plants through a variety of mechanisms including by triggering natural plant resistance to diseases and stresses, and through competitive exclusion of other pathogens.

*Clonostachys* reproduces by means of large numbers of microscopic (5-7 µM) bean-shaped spores. When applied to plants, the spores germinate to produce tiny tubes from which extremely fine branches form and penetrate into the plant tissues. Penetrations can occur on living petals, leaves, plant wounds, roots, tubers and other parts of plants. Once inside the tissues, each branch forms a microscopic fungal colony. Plants with *Clonostachys* colonies show no symptoms such as those produced by disease-causing organisms (pathogens). When established as an endophyte inside the plant tissues *Clonostachys* can exert beneficial effects such as triggering natural plant resistance to diseases and stresses.

The relationship of microscopic *Clonostachys* colonies with the plant tissues changes abruptly when the plant tissues begin to senesce, such as when a leaf first starts to turn yellow or when a disease or stress begins to develop. At that time, the tiny colonies begin to grow rapidly and often fully occupy neighbouring tissues. *Clonostachys* begins this growth before almost all other fungi and bacteria that grow on senescing and dying plants. Thus *Clonostachys* is a pioneer colonizer of senescing plant tissues. In effect, it occupies the tissues ahead of other organisms including destructive pathogens such *Botrytis, Sclerotinia* and *Monilinia*. Once the tissues are occupied, other organisms including pathogens do not displace the occupying organism. *Clonostachys* is able to block growth of pathogens and other fungi simply by pre-emptive occupation of the tissues. This competitive exclusion is a principal means by which *Clonostachys* suppresses disease organisms and disease development in plants. As shown in the Examples, *Clonostachys* BVT Cr-7 is particularly effective in controlling diseases and pathogens is a wide variety of plants.

*Clonostachys* produces spores when the colonized tissues progressively senesce and die. In many instances such spores initiate new cycles of endophytic growth in nearby living plants. *Clonostachys* is able to persist for a while in dead plant materials which it colonized while they were alive. However, it has little ability to grow on dead plant materials already occupied by other fungi and bacteria. In this kind of situation *Clonostachys* does not compete well against microbes such as *Penicillium* and *Aspergillus* which are adapted to microbial world of plant residues and soils.

*Clonostachys* also has the ability to grow on the hyphae and mycelia of other fungi (i.e. is a mycoparasite). *Clonostachys* usually attacks another fungus only after making very close contact with the hyphae, sclerotia or other part of the fungus (i.e absolute contact or at a distance of perhaps 1-5 µM). In doing so the *Clonostachys* hyphae sometimes coil around the fungus being parasitized and the "host fungus" essentially dies.

Without being limited by theory, the principal ways by which *Clonostachys* suppresses pathogens and diseases in plants is thought to be by: A. rapidly occupying senescing or damaged tissues so as to preclude growth of pathogens in the tissues; and B, by stimulating natural resistance mechanisms of plants to disease organisms. Further, *Clonostachys* is able to inactivate or kill survival structures of fungi (such as sclerotia and various kinds of spores in or on soils) through parasitism (i.e. growing on them as food sources). BVT Cr-7 is an isolated strain of *Clonostachys* that exhibits a number of characteristics that make it particularly effective as a biological control agent for the treatment of plants.

Properties and Characteristics of Strain BVT Cr-7

In one embodiment, there is provided an isolated strain of *Clonostachys*, termed BVT Cr-7. In one embodiment, the strain is that deposited under accession number 040913-01 at the International Depository Authority of Canada located in the National Microbiology Laboratory, Public Health Agency of Canada, 1015 Arlington Street, Winnipeg, Manitoba, R3E 3R2, Canada on Sep. 4, 2013. In one embodiment, "*Clonostachys rosea f. rosea* strain BVT Cr-7" or "BVT Cr-7" includes any cultures, spores, cells and progeny produced from said strain such as by asexual reproduction. As described herein, BVT Cr-7 exhibits a number of advantageous properties over other strains of *Clonostachys*.

For example, in one embodiment BVT Cr-7 is able to produce spores on standard agar media and plant seeds such as sterilized cereal seeds. In one embodiment, BVT Cr-7 has an improved ability to produce spores on standard agar media and plant seeds such as sterilized cereal seeds compared to other strains of *Clonostachys rosea f. rosea*, such as 88-710 (otherwise known as AFr-710, PG-710). Strain 88-710 is described in Sutton et al., *Evaluation of the Fungal Endophyte Clonostachys rosea as an Inoculant to Enhance Growth, Fitness and Productivity of Crop* Plants. Proc. IV$^{th}$ IS on Seed, Transplant and Stand Establishment of Hort. Crops Ed.: D. I. Leskovar, Acta Hort. 782, ISHS 2008 pp. 279-286 (hereby incorporated by reference in its entirety). In one embodiment, the cereal seeds are wheat or barley seeds. In one embodiment, BVT Cr-7 is useful for the production of an inoculant for use in the treatment of plants.

In one aspect, BVT Cr-7 is able to establish endophytically in plants. In one embodiment, BVT Cr-7 is able to establish endophytically in the roots of plants, such as the roots of plant crops. In one embodiment, BVT Cr-7 has an improved ability to establish endophytically in the roots of plants compared to other strains of *Clonostachys rosea f. rosea*, such as 88-710. For example, in one embodiment BVT Cr-7 has an improved ability to establish endophytically in plant crops and/or plants such as small grained cereals, turf grasses, peas, canola, soybeans, peppers, tomatoes and cucumbers.

In one embodiment, BVT Cr-7 is able to establish endophytically in the foliage and/or flowers of plants. In one embodiment, BVT Cr-7 has an improved ability to establish endophytically in the foliage and flowers of plants compared to other strains of *Clonostachys rosea f. rosea*, such as 88-710. For example, in one embodiment BVT Cr-7 has an improved ability to establish endophytically in the foliage and/or flowers of mini roses, strawberries, sunflowers, and canola.

In another aspect, BVT Cr-7 is able to suppress and/or control disease in plants. In one embodiment, BVT Cr-7 is able to suppress and/or control disease in plants caused by pathogens such as other fungi or microorganisms. In one embodiment, BVT Cr-7 has an improved ability to suppress or control diseases in plants other compared to other strains of *Clonostachys rosea f. rosea*, such as 88-710. For example, in one embodiment, BVT Cr-7 has an improved ability to suppress or control diseases that affect the foliage, flowers, fruits and/or roots of plants. In one embodiment, the disease is caused by *Botrytis cinerea* (grey mold diseases), *Sclerotinia sclerotiorum* (white mould diseases) and/or by species of *Pythium* spp., *Rhizoctonia*, and/or *Fusarium* (root rots and other diseases).

In one embodiment, BVT Cr-7 is able to reduce spoilage of plant materials. For example, in one embodiment, contacting harvested plant material with BVT Cr-7 such as by spay treatment reduces the incidence of rot relative to untreated plant material.

Application of BVT Cr-7 to Plants and/or Parts Thereof

In one embodiment, the methods and uses described herein include contacting a plant or plant material with BVT Cr-7. In one embodiment, BVT Cr-7 is exposed to plants or plant material such as to encourage the endophytic colonization of the plants or plant material. BVT Cr-7 may be applied to any part of a plant including plant foliage, flowers, roots, tubers and/or seeds by any known method, including through sprays, mists, by dipping, through nutrient solutions, and/or through insect vectoring depending on the application.

For example, young plants for transplanting can be treated by drenching the soil medium or dipping the plants at transplanting.

In another example, diseases caused by flower infecting pathogens can often be effectively controlled by applying *Clonostachys rosea* BVT Cr-7 to the flowers such as by spray treatments or insect vectoring, such as bee-vectoring technology as described in PCT Publication No. WO2012/135940 and PCT Application No. PCT/CA2013/050179, the contents of which are hereby incorporated by reference in their entirety. In one embodiment, bee vectoring allows for the treatment of flowering crops because the bees deliver *Clonostachys* to freshly opened flowers each day (in contrast to, for example, weekly sprays).

Other exemplary applications include application of *Clonostachys* to foliage of greenhouse crops by ultra low volume misting or conventional spraying to control pathogens such as *Botrytis* on the leaves and in stem wounds made during de-leafing and other pruning practices; spray treatments of grasses on golf courses with *Clonostachys* to control dollar spot (*Sclerotinia*), snow molds (*Typhula, Microdochium*) and other foliage diseases; application of *Clonostachys* to fresh wounds (within 48 hours) often provides long term protection against many wound-infecting disease organisms, for example in grafting, cuttings, and injured plants; and seeds may be treated with *Clonostachys* (followed by growth of the fungus in the root systems) to enhance the ability of crops such as field peas to sustain growth when stressed by drought or production practices (including use of certain pesticides).

In one embodiment, BVT Cr-7 as described herein may be useful for controlling pathogens such as *sclerotinia sclerotiorum, monilinia vaccinii-corymbosi,* and/or *botrytis cinerea* in various crops, including canola, sunflower, raspberry, blueberry, strawberry, apple, pear, kiwi, watermelon, coffee, mango, avocado, cherry, plum, almond, peach, cashew, guava, alfalfa, buckwheat, clover, bean, pea, onion, soybean, cotton, mustard, blackberry, gooseberry, pepper, eggplant, and currant.

In some embodiments, BVT Cr-7 is applied to plants as a single dose exposure or in multiple doses or exposures at different times. For example in one embodiment, plants are dosed or exposed to BVT Cr7, such as by spraying or insect vectoring with a bee hive equipped with a suitable inoculum dispenser at least 2 days, 4 days, 1 week, 2 weeks, 1 month or greater than 1 month apart.

In one embodiment, plants are contacted with BVT Cr-7 one or more times during the yearly growing cycle of the target plant. For example, in one embodiment, BVT Cr-7 is applied to plants in the spring at the start of the growing season and/or in the fall at the end of the growing season. In one embodiment, BVT Cr-7 is applied to plants before harvest of plant materials, such as 1 week, 2 week, 3 weeks or 4 weeks before the harvest of plant materials.

Formulations for Inoculating Plants

In one aspect, there is provided a formulation comprising BVT Cr-7 that is suitable for inoculating plants or plant materials. Optionally, the formulation may be a solid such as a powdered formulation, or a solution such as an aqueous solution. In one embodiment, the formulation comprises freeze-dried spores of BVT Cr-7. In one embodiment, the formulations described herein are useful as an inoculant for the treatment of plants.

In one embodiment, the formulation may include various additives combined with an isolated culture or fungal spores derived from *Clonostachys rosea f. rosea* strain BVT Cr-7.

A skilled person will appreciate that the concentration of cells or spores in the formulation may vary depending on the conditions in which the formulation is to be used (e.g. climate, target plant, method of applying the formulation to the plants or plant materials etc.).

In some embodiments, the formulation is a solid formulation and may comprise between about $1 \times 10^8$ and about $4 \times 10^8$ spores per gram of formulation, optionally between about $2 \times 10^8$ and about $4 \times 10^8$ spores per gram of formulation.

In some embodiments, the additives include one or more of a stabilizing agent, a moisture absorption agent, an attracting agent, a diluent, and/or an anti-caking agent. In some embodiments, the additives may include two or more of a stabilizing agent, a moisture absorption agent, an attracting agent, a diluent, and/or an anti-caking agent. In one embodiment, the formulation is suitable for insect vectoring, such as that described in PCT/CA2013/050179, hereby incorporated by reference.

In one embodiment, the formulation includes a stabilizing agent. The stabilizing agent serves to prevent or minimize decay, breaking down, or activation of the fungal spore prior to delivery to the plant target. Examples of stabilizing agents include particulate calcium silicate. For example, in some embodiments, the formulation may comprise a fungal spore, and the fungal spore may be bonded to at least some of the calcium silicate. The formulation may have a density of between about $1 \times 10^9$ and $4 \times 10^9$ spores per gram of calcium silicate to which it is bonded. In one embodiment, the formulation may have about $2 \times 10^9$ spores per gram of calcium silicate to which it is bonded.

In one embodiment, the formulation includes a moisture absorption agent. The moisture absorption agent serves to absorb moisture from the formulation in order to keep the formulation relatively dry and to prevent caking or clumping of the formulation. Examples of moisturizing agents include dessicants, such as particles or beads of silica gel, and super absorbent polymers, such as sodium polyacrylate. Further examples of moisture absorption agents include wood shavings, and clay balls.

In one embodiment, the formulation includes an attracting agent. The attracting agent may help to attract the formulation to plants and/or vectoring insects. For example, the attracting agent may have a net positive electrostatic charge, so that it is electrostatically attracted to plants and/or vectoring insects, which have a net negative electrostatic charge. In some examples, the attracting agent may include a mineral, or a mixture of minerals. In one particular example, the attracting agent may include a mineral mixture sold by Agri-Dynamics (Martins Creek, Pa.) under the name DYNA-MIN™, which includes the following minerals: silicon dioxide, aluminum oxide, calcium, iron, magnesium, potassium, sodium, phosphorus, titanium, manganese, strontium, zirconium, lithium, rubidium, boron, zinc, vanadium, chromium, copper, yttrium, nickel, cobalt, gallium, cesium, scandium, tin, molybdenum, and additional trace elements. In another example, the attracting agent may include calcium limestone.

In one embodiment, the formulation includes a diluent. The diluent may be a suitable starch or flour. In examples wherein the formulation is to be delivered by insect vectoring, the diluent may be selected so that it does not irritate or harm the insects, and will not be eaten by the insects. The diluent may further be selected so that it does not absorb significant amounts of moisture, so that the diluent does not clump. Examples of diluents which may be suitable for insect vectoring include corn flour, and grain flours such as rye, wheat, rice flour, and spelt flour. In alternate examples, the diluent may be kaolin. In other examples the diluent may comprise milk powder or talc. These may be particularly useful in examples wherein the formulation is delivered in a manner other than insect vectoring, such as by spraying.

In one embodiment, the formulation includes a suitable anti-caking agent. One particular example of an anti-caking agent is magnesium oxide. Other anti-caking agents known those skilled in the art may also be employed in the formulations described herein.

In one embodiment, the formulation is a liquid formulation, such as an aqueous suspension. In one embodiment, the formulation comprises about 1 to $6 \times 10^5$ spores/mL and optionally about 2 to $5 \times 10^5$ spores/mL. In one embodiment, the formulation is a liquid formulation and comprises one or more agriculturally suitable carriers or diluents. In one embodiment, the liquid formulation comprises one or more stabilizing agents.

Also provided are methods for the production of a biological control agent as described herein, such as an inoculant comprising an effective amount of BVT Cr-7. For example, in one embodiment there is provided a method comprising providing an isolated culture of BVT Cr-7; inoculating a substrate with the isolated culture of BVT Cr-7 and incubating the substrate under conditions suitable for fungal growth. In one embodiment, the inoculated substrate is incubated at a relative humidity of greater than 90% or greater than 95% and at a temperature in the range of 20-24 degrees Celsius.

In one embodiment, the substrate is a sterile substrate. In one embodiment, the method further comprises incubating the substrate under conditions suitable for fungal sporulation. Conditions suitable for fungal sporulation of *Clonostachys rosea* are known in the art. For example, in one embodiment, the conditions suitable for fungal sporulation include growing BVT Cr-7 on a substrate such as sterilized seeds at about 20-24 degrees Celsius at high levels of humidity (greater than about 95%) for a few days to allow for growth of the fungus before reducing the relative humidity to less than about 50%, optionally about 20-50%, 35-45%, or about 20-25% for at least 10 days, at least 2 weeks or greater than 2 weeks to favour abundant spore production. The inventors have determined that reducing the relative humidity level to about 35-45% for least about 2 weeks is particularly effective for the production of fungal spores of BVT Cr7. In one embodiment, the sterilized seeds are barley seeds. In one embodiment, the substrate is aerated throughout spore production. Preferably, the substrate is incubated under sterile conditions to avoid contamination with other microbes.

In one embodiment, the method further comprises removing the spores from the substrate, optionally by suspension in an aqueous solution. In one embodiment, the spores are removed from the substrate to produce an inoculum. Optionally, the spores may be removed from the substrate and then freeze dried or otherwise processed as known in the art to produce a biological control agent. In one embodiment, the method comprises mixing the inoculum with one or more additional ingredients such as a stabilizing agent, a moisture absorption agent, an attracting agent, a diluent, and/or an anti-caking agent to produce a formulation as described herein. In one embodiment, the method comprises removing the spores from the substrate by admixture of the substrate with sterile water. In one embodiment, the method comprises shaking the mixture, filtering out clumped or course materials, gently centrifuging the filtrate and resuspending the pelleted material to produce an aqueous solution.

Additional Embodiments

In one embodiment there is provided a method of controlling plant pathogens comprising administering BVT Cr-7 as described herein to a plant or plant material. For example, BVT Cr-7 isolates, spores and formulations as disclosed herein may be used as a prophylactic agent to diminish the chance of an infection occurring in plants or plant material, particularly an infection by a pathogenic fungus such *Botrytis* or *Sclerotinia*.

Also provided is a method for controlling pathogens in plants, the method comprising treating a batch of seeds with the cultures or formulations disclosed herein and then culturing the treated seeds into plants.

Also provided is a formulation comprising BVT Cr-7 as described herein and a carrier or diluent, and optionally further comprising an additional biocontrol agent such as an antifungal agent or pesticide. The formulation may be a seed treatment formulation, plant treatment formulation, or a soil treatment formulation. In one embodiment, the carrier or diluent is an agriculturally acceptable carrier or diluent that helps ensure stability and performance of the formulation. In one embodiment, the carrier or diluent is compatible with the biological control agent, agriculturally acceptable and has a good absorptive capacity and a suitable bulk density, allowing easy particle dispersion and attachment.

The formulations described herein containing BVT Cr-7 may, for example, be applied to the seeds or propagules of the plants, to the growth medium (e.g. soil or water), to the roots of plants and/or to the foliage of the plants, to the flowers or pistils of the plants, or to any combination thereof. Exemplary plants that can be treated with the present formulations include, but are not limited to agricultural crops such as seed crops, grain crops, fibre crops, pulse crops, horticultural crops, forestry crops, and turf grasses.

The formulations comprising BVT Cr-7 described herein may be applied to a plant in aqueous sprays, granules and dust/powder formulations in accordance with established practice in the art. An aqueous spray is usually prepared by mixing a wettable powder or emulsifiable concentrate formulation of an isolated culture or spores of BVT Cr-7 with a relatively large amount of water to form a dispersion.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Isolation of *Clonostachys rosea f. Rosea* Strain BVT Cr-7

Several kinds of crop plants (wheat, soybeans, corn, alfalfa, grasses) were collected in fields near Guelph, Ontario as possible sources of new strains of *Clonostachys roseum f. roseum*. The strain of the fungus described herein as BVT Cr-7 was isolated from a root of a healthy young wheat plant (early tillering stage) taken from a field near Arkell, Ontario. A series of other strains of *Clonostachys rosea f. rosea* (BVT Cr-1 through BVT Cr-14) were also isolated as set out below.

The procedure used to isolate *Clonostachys* strains from roots of wheat plants and other crops was as follows. Aseptic techniques were employed throughout. Roots from several plants were washed in tap water to remove soil, blotted dry on paper towels and then cut into segments 1-2 cm long. The segments were blotted dry with paper tissues and incubated on Paraquat-chloramphenicol agar medium in Petri dishes at 20-22° C. The Paraquat accelerates root senescence, which allows *Clonostachys* to sporulate relatively quickly (e.g. within 6-8 days) on surfaces of roots which it had previously colonized. The sporulation structures (conidiophores and the conidia they bear) are the basis for the fungus to be recognized and identified. The conidia (i.e. spores) can be removed and germinated in culture.

To isolate the fungus, spores were transferred on a sterile needle from conidiophores on the roots to potato dextrose agar (PDA) medium amended with streptomycin (to suppress bacteria) in Petri dishes. After the spores had germinated and produced colonies on the agar medium, the fungus was sub-cultured onto PDA-streptomycin in Petri dishes. Spores of subcultures were suspended in sterile-distilled water, and the suspensions were serially diluted and spread onto PDA. Colonies growing from single spores were transferred to fresh agar medium in Petri dishes and maintained in culture at 4° C. as a series of isolates for further characterization as possible biological control agents.

The series of isolated strains were then tested and compared to each other and to established strains of *Clonostachys rosea f. rosea* including 88-710 and EV-1a. Strain 88-710 is described in Sutton et al., *Evaluation of the Fungal Endophyte Clonostachys rosea as an Inoculant to Enhance Growth, Fitness and Productivity of Crop Plants.* Proc. IV$^{th}$ IS on Seed, Transplant and Stand Establishment of Hort. Crops Ed.: D. I. Leskovar, Acta Hort. 782, ISHS 2008 pp. 279-286 (hereby incorporated by reference in its entirety).

The isolated strain BVT Cr-7 [Bee-Vectoring Technology *Clonostachys rosea* #7] was then identified as a superior isolate through experimentation as set out in Examples 2 and 3. Isolated cultures of BVT Cr-7 were then maintained and deposited under accession number 040913-01 at the International Depository Authority of Canada located in the National Microbiology Laboratory, Public Health Agency of Canada, 1015 Arlington Street, Winnipeg, Manitoba, R3E 3R2, Canada on Sep. 4, 2013.

Example 2

Testing and Characterization of BVT Cr-7 Relative to other Strains of *Clonostachys rosea f. Rosea*

The newly isolated strain BVT Cr-7 and two additional strains of *Clonostachys rosea f. rosea* (88-710 and EV-1a) were compared in a series of experiments designed to evaluate their properties as biological control agents for the treatment of plants. BVT Cr-7 was observed to be equivalent or superior compared to 88-710 and/or EV-1a based on each of the following criteria:

- Growth and abundance of spore production on standard agar media and on substrates such as sterilized cereal seeds (wheat and barley) that can be used for commercial inoculum production.
- Ability to establish abundantly inside the roots (i.e. endophytically) of diverse kinds of crop plants including small grained cereals, turf grasses, peas, canola, soybeans, peppers, tomatoes and cucumbers.
- Ability to establish endophytically in the foliage and flowers of several test plants (mini roses, strawberries, sunflowers, canola).
- Ability to suppress or control a wide spectrum of destructive diseases that affect affecting the foliage, flowers, fruits and roots, especially those caused by *Botrytis cinerea* (grey mold diseases), *Sclerotinia sclerotiorum* (white mould diseases) and by species of *Pythium* spp., *Rhizoctonia*, and *Fusarium* (root rots and other diseases).

BVT Cr-7 therefore exhibits a desired performance profile against diverse diseases in diverse kinds of crops and generally exhibits preferably activity as a biological control agent compared to 88-710 and/or EV-1a.

Example 3

Performance of BVT Cr-7 for Controlling Disease in Plants

BVT Cr-7 was applied to a series of plants and crops in order to evaluate its activity in field trials. In particular, BVT Cr-7 was applied to flowers of the following plants (such as via bee vectors or spray treatments) to control diseases caused by the particular pathogens:

SUNFLOWERS: *Sclerotinia, Botrytis*, and *Fusarium*
CANOLA: *Sclerotinia*
BLUEBERRIES: *Monilinia, Sclerotinia, Botrytis* and *Phomopsis*
STRAWBERRIES: *Botrytis, Phomopsis*, and *Rhizopus*
RASPBERRIES: *Botrytis*
GRAPES: *Botrytis, Phomopsis*

BVT Cr-7 was also applied to the roots of greenhouse hydroponic crops (via a nutrient solution) and was observed to control diseases caused by *Pythium* and *Fusarium* in peppers, cucumbers and tomatoes.

BVT Cr-7 was applied to the foliage (as a spray) of turf grasses, greenhouse peppers and greenhouse tomatoes. BVT Cr-7 was observed to control diseases caused by *Sclerotinia, Typhula*, and *Microdochium* in Turf grasses, *Fusarium* in greenhouse peppers and *Botrytis* in greenhouse tomatoes.

Field Trial of BVT Cr-7 for the Treatment of Strawberries

A trial was conducted in Ontario in which four colonies of bumble bees were positioned at the centre of a four-acre organic strawberry field. Each colony box ("hive") was equipped with a dispenser to dust the bees with a powder formulation of BVT Cr-7 when they exited the hives. BVT Cr-7 was recovered from more than 80% of the strawberry flowers across the field. Levels of fruit rot in BVT Cr-7 bee-vectored field were extraordinarily low compared to a nearby organic strawberry field that was untreated. In this trial BVT Cr-7 suppressed *Botrytis* berry rot by >90%, *Phomopsis* berry rot by 100%, and *Rhizopus* rot ("leak") by 93%.

Field Trial of BVT Cr-7 for the Treatment of Sunflowers

A field vectoring test of BVT Cr-7 by bumble bees was conducted in sunflowers near Ripley Ontario. Harvested seeds from the treated field and from a control field in the area (no bumble bees or BVT Cr-7) were compared in lab assays. Germination of seeds from the bee-vectored treatment was 27% higher than in the control seeds (i.e. 89.7% compared to 70.7%). The BVT Cr-7 treatment also reduced the level of several undesirable moulds on the seeds (*Fusarium*, *Botrytis*, and *Penicillium*).

Bumble bees strongly vectored BVT Cr-7 at least 360 m from hives to the flowers. BVT Cr-7 effectively established as an endophyte in large proportions of the florets and seeds of the sunflower heads. The destructive pathogen *Sclerotinia* was not found on sunflower heads colonized by BVT Cr-7, but was present on 20-25% of heads outside the range of bee vectored BVT Cr-7. Growers reported that seed yields increased more than 20% (influence of pollination plus BVT Cr-7) and better quality especially greater seed size (and therefore more oil) and reductions in moulds on harvested seeds.

Field Trial of BVT Cr-7 for the Treatment of Blueberries

Trials in Prince Edward Island demonstrated that BVT Cr-7 applied by bumble bees as a powder formulation or as sprays of spore suspensions in water can establish endophytically in the flowers, berries and foliage of low bush blueberries. The treatments increased the proportion of healthy berries by 70-100%. BVT Cr-7 strongly reduced incidence of mummy-berry, a major blueberry disease caused by the fungus *Monilinia vaccinii-corymbosi* including when weather conditions were extremely favourable for the disease. BVT Cr-7 also markedly reduced browning and premature dropping of berries which we found to be due to a disease hitherto not described and caused by *Sclerotinia sclerotiorum*. In one year of the trial, the *Sclerotinia* disease was at least as damaging as mummy-berry in untreated blueberries. Appropriately timed spray applications of BVT Cr-7 were effective against *Phomopsis* canker in low-bush blueberries and in a trial in high-bush blueberries in Ontario. Thus BVT Cr-7 is a broad-spectrum biological control tool against the major diseases that affect blueberries in the field.

*Clonostachys rosea f. rosea* strain BVT Cr-7 is therefore able to control a wide spectrum of diseases of major economic importance in numerous kinds of crops.

Example 4

Performance of BVT Cr-7 in Controlled Conditions

BVT Cr-7 was tested on a number of specific crops in order to evaluate its use as a biological control agent:

A. CANOLA SEEDLINGS: Seed treatment with BVT Cr-7 gave very strong suppression of a highly aggressive strain of *Rhizoctonia solani* in a sterilized soil and of *Pythium* root rot in a field soil.

B. HARVESTED CARROTS (ROOTS): BVT Cr-7 greatly suppressed *Sclerotinia* rot when co-inoculated with the pathogen on carrots in simulated storage.

C. BROCCOLI heads: Spray treatment with BVT Cr-7 controlled *Alternaria*, *Cladosporium* and premature discoloration of stored broccoli heads.

D. PEACHES: Mist application of BVT Cr-7 to fresh peaches significantly suppressed incidence and rate of development of brown rot (*Monilia*) in the fruit.

E. *MISCANTHUS*: Dipping of the rhizomes of *Miscanthus* in a spore suspension of BVT Cr-7 prior to storage provided protection against rots due to *Pythium*, *Fusarium* and *Rhizoctonia* during several months of cold storage.

Based on these results BVT Cr-7 has demonstrated broader proven high performance disease resistance under diverse conditions in more kinds of crops than other strains of *C. rosea f. rosea*.

Example 5

Treatment of Greenhouse Tomatoes Using BVT Cr-7

Greenhouse tomato flowers treated with *Clonostachys rosea* BVT-Cr7 and untreated control flowers, were assessed for *Clonostachys rosea*, *Botrytis cinerea* and common moulds.

*C. rosea* BVT Cr-7 was delivered to plants using bee vectoring by equipping a colony box (bumble bee hive) with an inoculum dispenser in order to deliver the inoculum to flowers of tomatoes in a relatively small commercial greenhouse (less than a quarter acre) at a test site in Nova Scotia, Canada.

Laboratory Procedures

Samples of tomato flowers were received in excellent condition from the test site. Each sample comprised four flowers in a small plastic bag. The four flowers of each sample were placed on Paraquat-chloramphenicol agar (PCA) medium in Petri dishes on 20 Jun. 2014 and incubated in clear plastic boxes at 21-25° C. in subdued daylight for 7 days. Each flower was then assessed microscopically for *Clonostachys rosea*, *Botrytis cinerea* and common moulds. Paraquat accelerates natural senescence of plant tissues and thereby allows *Clonostachys rosea* to produce spores and thus be identified. Other fungi can also grow and sporulate on the tissues as they senesce and die.

Results

As shown in Table 1, sporulation of the biological control agent *Clonostachys rosea* BVT Cr-7 was observed on 87.5% of the treated flowers and 0% of the untreated flowers. Sporulation of *C. rosea* on the clusters of stamens plus pistils of treated flowers was dense and extensive in almost all instances, such that the cone-like form of these clusters appeared almost entirely white. Sporulation on the petals of most treated flowers was moderate to heavy.

Sporulation of the pathogen *Botrytis cinerea* was found on 12% of untreated flowers (and was light in all instances) and 0% of flowers treated with *C. rosea*.

Common greenhouse moulds were observed at varying degrees on the samples. Principally these included species of *Cladosporium* (not *Fulvia fulvum*), *Aspergillus*, and *Penicillium*, *Alternaria alternata* and a fungus resembling *Acremonium*. To provide quantitative information on the effects of *C. rosea* on these molds, each flower was assessed for "Moulds" (i.e. any fungi other than *C. rosea* or *Botrytis*) on a scale of 1-5 presented in Table 1, with 1 representing zero-trace of mould and 5 representing very heavy mould. Areas of the flowers with sporulation of these moulds were very low (mean rating 1.80/5.00) in flowers in which *C. rosea* was established and sporulating but high (4.55/5.00) in the absence of *C. rosea* (including all flowers of the controls). The biological control agent BVT Cr-7 was therefore observed to markedly suppress these moulds in addition to *Botrytis*. Essentially the plated flowers of the *C. rosea* treatment appeared very "clean" compared to the untreated flowers.

TABLE 1

Results from trials of BVT Cr-7 dispersed using bee vectoring in a greenhouse.

| | Flowers treated with BVT-Cr7 | | | Untreated Control Flowers | | |
|---|---|---|---|---|---|---|
| Sample No. | BVT-Cr7+ out of 4 | Mould Rating* | Total | Mould Rating* | Total | B. cinera |
| 1 | 4 | 1, 1, 1, 1 | 4 | 5, 5, 5, 5 | 20 | |
| 2 | 3 | 1, 1, 1, 3 | 6 | 3, 5, 5, 5 | 18 | |
| 3 | 4 | 1, 1, 1, 1 | 4 | 5, 5, 4, 4 | 18 | ++ |
| 4 | 4 | 3, 2, 1, 1 | 7 | 5, 5, 5, 4 | 19 | |
| 5 | 3 | 1, 1, 3, 2 | 7 | 5, 5, 5, 5 | 20 | + |
| 6 | 4 | 1, 1, 4, 1 | 7 | 5, 5, 5, 5 | 20 | |
| 7 | 2 | 4, 3, 1, 2 | 10 | 5, 4, 5, 4 | 18 | |
| 8 | 4 | 1, 2, 1, 4 | 8 | 3, 5, 5, 4 | 17 | |
| 9 | 4 | 1, 4, 2, 2 | 9 | 5, 5, 5, 5 | 20 | |
| 10 | 3 | 3, 1, 1, 2 | 7 | 2, 5, 5, 5 | 17 | + |
| 11 | 3 | 5, 1, 1, 1 | 8 | 5, 5, 5, 5 | 20 | |
| 12 | 4 | 2, 3, 2, 4 | 11 | 5, 3, 5, 5 | 18 | + |
| 13 | 3 | 1, 1, 4, 1 | 7 | 5, 5, 5, 5 | 20 | + |
| 14 | 4 | 1, 3, 1, 1 | 6 | 5, 5, 5, 5 | 20 | + |
| 49/56 = 87.5% | | Total | 101 | Total | 255 | 7 |
| | | Mean rating per flower | 1.80 | | 4.55 | |

*The scale for area of plated flowers covered with one or more of these moulds was: 1 = zero-trace; 2, light; 3, moderately light; 4, moderately heavy; 5, very heavy.

Remarkably, the use of bee vectoring to deliver BVT-Cr7 inoculum allowed rapid and thorough endophytic establishment of the biological control agent in the flowers as judged by the remarkable sporulation levels observed after the flowers had been incubated for a week on PCA.

Excellent establishment of *C. rosea* in clusters of "stamens plus style" was observed and is of particular importance given that these are principal portals of entry of pathogens.

The apparent complete suppression of *B. cinerea* and major suppression of diverse greenhouse moulds in flowers colonized by *C. rosea* was observed indicating the broad spectrum capabilities and activity of the BVT Cr-7 against other fungi (such as by competitive exclusion).

While the present disclosure has been described with reference to what are presently considered to be the preferred examples, it is to be understood that the application is not limited to the disclosed examples. To the contrary, the disclosure is intended to cover various modifications and equivalent arrangements included within the spirit and scope of the appended claims.

All publications, patents, patent applications and biological deposits are herein incorporated by reference in their entirety to the same extent as if each individual publication, patent, patent application or biological deposit was specifically and individually indicated to be incorporated by reference in its entirety.

The invention claimed is:

1. A method of treating a plant comprising contacting the plant with a biological control agent comprising an isolated culture of fungus *Clonostachys rosea f. rosea* strain deposited under accession number IDAC 040913-01, or a fungal spore thereof.

2. The method of claim 1, wherein said contacting improves the health, growth and/or yield of the plant.

3. The method of claim 1 wherein said contacting prevents or treats disease in the plant.

4. The method of claim 1, wherein said contacting controls growth of mold or plant pathogens on the plant.

5. The method of claim 1, wherein said contacting improves germination of plant seed.

6. The method of claim 3, wherein the pathogen is *Botrytis cinema, Sclerotinia sclerotiorum, Pythium* spp., *Alternaria, Monilia, Monilinia, Colletotrichm, Cladosporium Rhizoctonia, Streptomyces, Didymella* and/or *Fusarium.*

7. The method of claim 3, wherein the disease is grey mold disease, white mold disease, brown rot, root rot and/or phomopsis.

8. The method of claim 1, wherein the plant is selected from sunflowers, canola, blueberries, strawberries, grapes, peppers, cucumbers, tomatoes, turf grasses, peppers, tomatoes, broccoli, peaches, canola seedlings, and/or miscanthus.

9. The method of claim 1, wherein the plant is grown in a greenhouse.

10. The method of claim 1, wherein contacting the plant with the biological control agent comprises applying a spray, a mist, a dip, or a nutrient solution to the plant.

11. The method of claim 1, wherein contacting the plant with the biological control agent comprises insect vectoring.

12. A method to reduce the spoilage of plant material, the method comprising contacting the plant material with a biological control agent comprising an isolated culture of fungus *Clonostachys rosea f. rosea* strain deposited under accession number IDAC 040913-01, or a fungal spore thereof.

13. The method of claim 12, wherein the plant material has been harvested.

14. A method for the production of a fungal *Clonostachys rosea f. rosea* biological control agent, the method comprising:

inoculating a substrate with an isolated culture of fungus *Clonostachys rosea f. rosea* strain deposited under accession number IDAC 040913-01; and incubating the substrate under conditions suitable for fungal growth to produce the fungal *Clonostachys rosea f. rosea* biological control agent wherein the conditions suitable for fungal growth comprise a relative humidity of greater than 95% and a temperature in the range of 20-24 degrees Celsius.

15. The method of claim 14, further comprising incubating the substrate under conditions suitable for fungal sporulation, wherein the conditions suitable for fungal sporulation comprise reducing the relative humidity to less than about 50%.

16. The method of claim 15, further comprising removing the spores from the substrate to produce an inoculum and mixing the spores with a diluent.

17. The method of claim 1, wherein the biological control agent is a liquid formulation.

18. The method of claim 1, wherein the biological control agent is a solid formulation.

19. The method of claim 18, wherein the solid formulation comprises a stabilizing agent, wherein the stabilizing agent is particulate calcium silicate.

20. The method of claim 1, wherein the biological control agent is a formulation comprising at least $1\times10^8$ fungal spores of *Clonostachys rosea f. rosea* per gram of formulation.

21. The method of claim 1, wherein the biological control agent is a formulation comprising at least $1\times10^9$ fungal spores of *Clonostachys rosea f. rosea* per gram of formulation.

* * * * *

UNITED STATES PATENT AND TRADEMARK OFFICE
CERTIFICATE OF CORRECTION

PATENT NO.         : 9,758,758 B2
APPLICATION NO.    : 15/021425
DATED              : September 12, 2017
INVENTOR(S)        : John Sutton and Todd Gordon Mason Page 1 of 1

It is certified that error appears in the above-identified patent and that said Letters Patent is hereby corrected as shown below:

In the Specification

At Column 1, Line 4, "filed Sep. 11, 2013, the contents" should read --filed Sep. 11, 2013 (now abandoned), the contents--.

In the Claims

In Claim 6 at Column 16, Line 4, "cinema" should read --cinerea--.

In Claim 6 at Column 16, Line 5, "Colletotrichm" should read --Colletotrichum--.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*